United States Patent [19]

Hazama et al.

[11] 4,169,207
[45] Sep. 25, 1979

[54] RACEMIZATION OF AN OPTICALLY ACTIVE LYSINE ALKYL ESTER

[75] Inventors: Motoo Hazama, Kyoto; Gohu Suzukamo, Ibaraki, both of Japan

[73] Assignee: Sumitomo Chemical Company, Limited, Osaka, Japan

[21] Appl. No.: 916,939

[22] Filed: Jun. 19, 1978

[30] Foreign Application Priority Data

Jun. 30, 1977 [JP] Japan ................................. 52-78654

[51] Int. Cl.$^2$ ..................... C07C 99/00; C07C 101/24
[52] U.S. Cl. ..................................... 560/169; 562/562
[58] Field of Search ................. 560/169; 562/562, 401

[56] References Cited

U.S. PATENT DOCUMENTS

| | | | |
|---|---|---|---|
| 2,536,360 | 1/1951 | Emmick | 562/401 |
| 2,586,154 | 2/1952 | Emmick | 562/401 |
| 3,297,637 | 1/1967 | Akabori | 562/401 |
| 3,970,700 | 7/1976 | Nagase | 260/570.8 R |
| 3,976,680 | 8/1976 | Clark | 562/401 |

FOREIGN PATENT DOCUMENTS

| | | | |
|---|---|---|---|
| 39-26386 | 11/1964 | Japan | 562/401 |
| 42-11923 | 7/1967 | Japan | 562/401 |
| 42-11924 | 7/1967 | Japan | 562/401 |
| 847785 | 9/1960 | United Kingdom | 562/401 |
| 1471389 | 4/1977 | United Kingdom . | |

*Primary Examiner*—James O. Thomas, Jr.
*Assistant Examiner*—Michael Shippen
*Attorney, Agent, or Firm*—Cushman, Darby & Cushman

[57] ABSTRACT

An optically active lysine alkyl ester.dihydrochloride is racemized by heating at 100° C. to 250° C. under an atmosphere of hydrogen. By combining this process with asymmetric hydrolysis of racemic lysine alkyl ester with enzymes, racemic lysine alkyl ester can be converted all to L-lysine.

7 Claims, No Drawings

RACEMIZATION OF AN OPTICALLY ACTIVE LYSINE ALKYL ESTER

This invention relates to racemization of optically active lysine esters. More particularly, this invention relates to a process for racemization of optically active lysine alkyl ester, which comprises heating an optically active lysine alkyl ester.dihydrochloride at 100° to 250° C. under an atmosphere of hydrogen.

Optically active lysine alkyl esters can be used as intermediates for organic industrial chemicals, agricultural or pharmaceutical materials and are also useful as optical resolution agents for racemic acids. In particular, L-lysine obtained by hydrolysis of L-lysine alkyl ester is one of essential amino acids, which is useful as food supplements.

According to conventional methods for synthesis of lysine alkyl esters, they are produced as racemic mixture and then subjected to optical resolution to give one useful optical isomer thereof. Accordingly, the residual optical antipode resulting from optical resolution is subjected to racemization, followed by repeated resolution, to be converted to useful optically active isomers. Thus, racemization is a very important technique.

The process according to the present invention also provides an important means, which enables conversion of all racemic lysine alkyl esters into L-lysine by combination with asymmetric hydrolysis with enzyme. That is, L-isomers of racemic lysine alkyl esters are preferentially hydrolyzed asymmetrically by enzymes having esterase activity to form L-lysine. After separation of the L-lysine formed, unaltered D-isomers or lysine alkyl esters containing excess of D-isomers are racemized by the process of the present invention to be converted to racemic lysine alkyl esters, which are contacted again with enzymes. By repeating this procedure, it is possible to convert racemic lysine alkyl esters all into L-lysine.

As racemization methods for optically active lysine, there have been known a number of methods such as a method by heating in the presence of water or improved methods thereof. (See, for example, Japanese patent examined publications No. 21231/1964, No. 26386/1964, No. 4011/73, Japanese patent unexamined publication No. 34817/1973). However, no satisfactory method for racemization of optically active lysine alkyl esters is available because of the difficulties that lysine alkyl esters are easily hydrolyzed into lysine in the presence of water and moreover they are not stable to bases or heat. The present inventors have made extensive studies about racemization of optically active lysine alkyl esters for the purpose as mentioned above. As the result, it has now been found that dihydrochlorides of optically active lysine alkyl esters can easily and quantitatively be converted to racemic mixture by heating at 100° to 250° C. in the presence of hydrogen.

In the present invention, the alkyl moiety of the optically active lysine alkyl esters may include lower alkyl having 1 to 4 carbon atoms such as methyl, ethyl, propyl or butyl. It is possible to racemize either D-isomer or L-isomer of the optically active lysine alkyl ester, or a mixture thereof with any optical purities of these isomers.

In practicing the process of the present invention, the presence of hydrogen is an important element. The reaction may be accelerated by increasing hydrogen pressure. For effective practice of the reaction, the hydrogen pressure is generally from 1 to 200 atm., preferably from 1 to 100 atm.

The present reaction may preferably be conducted in a suitable solvent. As solvents to be employed, there may preferably used alcohols corresponding to ester residues in the optically active lysine alkyl esters, i.e. methanol, ethanol, propanol or butanol, in order to obtain favorable results. Alternatively, there may also be used a mixture of such alcohols with other solvents which can dissolve the starting material, e.g. aromatic hydrocarbons such as benzene, toluene, etc., aliphatic hydrocarbons such as hexane or ethers such as tetrahydrofuran, dioxane, etc.

The reaction can effectively be carried at a temperature in the range from 100° to 250° C. At a temperature lower than the above temperature range, the reaction rate for racemization is too slow, while at a temperature exceeding by far the above temperature range racemization rate may be accelerated, but side reactions such as decomposition or others will be caused to give no advantage intended by the present reaction.

The reaction time varies depending on the reaction temperature and the hydrogen pressure as mentioned above. As the temperature is higher or the hydrogen pressure is higher, it is shortened. The reaction time may usually be from 10 minutes to 20 hours to accomplish the object, insofar as the reaction is performed within the temperature range and the pressure range as mentioned above.

The progress of the reaction can be followed by measurement of optical rotation at a certain concentration or by conventional analytical methods such as gas chromatography, NMR, etc. After completion of the reaction, the solvent is evaporated to give racemic lysine alkyl ester at a high purity.

The present invention is illustrated in further detail by the following Example, by which the present invention is not limited.

EXAMPLE 1

In a 100 ml reactor are charged 2.47 g (10 mmole) of L-lysine ethyl ester.dihydrochloride $\{[\alpha]_{546} = +13.2°$ (C=1, H$_2$O)$\}$ and 20 ml of dry ethanol and hydrogen is filled therein up to 50 atm. Then, the temperature is raised up to 170° C., at which stirring is continued by means of a magnetic stirrer for 6 hours. After the reaction, the mixture is cooled, followed by purging hydrogen and evaporation of the solvent, to recover 2.43 g of lysine ethyl ester.dihydrochloride (recovery=98.4%). This product has an optical rotation $[\alpha]_{546} = +0.6°$ (C=1, H$_2$O), showing that it is racemic mixture. The purity is found by GC analysis after trifluoroacetylation to be 96.1% lysine ethyl ester.

As impurities, there is observed no other impurity than lysine formed by partial hydrolysis. Examples 2–4.

Example 1 is repeated except that the reaction temperature, the reaction time and the hydrogen pressure are varied to give the results as shown in Table 1.

Table 1

| Example | Reaction temperature (°C.) | Reaction time (hr.) | Hydrogen pressure | Recovery (%) | $[\alpha]_{546}$ (C = 1, H$_2$O) |
|---|---|---|---|---|---|
| 2 | 170 | 3 | 50 | 98.5 | +2.6° |
| 3 | 150 | 8 | 50 | 96.0 | +3.6° |

Table 1-continued

| Example | Reaction temperature (°C.) | Reaction time (hr.) | Hydrogen pressure | Recovery (%) | $[\alpha]_{546}$ (C = 1, H$_2$O) |
| --- | --- | --- | --- | --- | --- |
| 4 | 170 | 8 | 5 | 96.4 | +5.2° |

EXAMPLE 5

Using 2.47 g (10 mmole) of D-lysine ethyl ester. dihydrochloride $\{[\alpha]_{546} = -10.5°$ (C=1, H$_2$O)$\}$ as the starting material, the reaction is carried out under the same conditions as in Example 2 to recover 2.46 g of lysine ethyl ester dihydrochloride (recovery=99.7%). This product has an optical rotation$[\alpha]_{546} = -2.5°$ (C=2.5, H$_2$O).

EXAMPLE 6

In a 100 ml reactor are charged 1.17 g (5 mmole) of L-lysine methyl ester.dihydrochloride $\{[\alpha]_{546} = +20.0°$ (C=1, H$_2$O)$\}$ and 20 ml of dry methanol, and hydrogen is filled therein up to 50 atm. Then, the temperature is raised up to 150° C., at which stirring is continued for 5 hours using a magnetic stirrer. After the reaction, the mixture is cooled, followed by purging hydrogen and evaporation of the solvent, to recover 1.10 g of lysine methyl ester.dihydrochloride(recovery=94.0%). This product has an optical rotation$[\alpha]_{546} = +2.0°$ (C=1, H$_2$O). After trifluoroacetylation, its optical isomer ratio D/L is determined by measurement of NMR in the presence of Europium opti-shift I (Euopt I: (perfluoroisopropyl camphorate)europium(III)] to be D/L=45/55.

REFERENCE EXAMPLE 1

The reaction is carried out in the same manner as in Example 1 except that nitrogen is filled to 1 atm. in place of hydrogen.

As the result, 2.47 g of lysine ethyl ester.dihydrochloride is recovered(recovery=100%). This product is found to have an otpical rotation$[\alpha]_{546} = +12.5°$ (C=1, H$_2$O).

REFERENCE EXAMPLE 2

The reaction is carried out in the same manner as in Example 6 except that nitrogen is filled to 1 atm. in place of hydrogen.

As the result, 1.17 g of lysine methyl ester.dihydrochloride is recovered(recovery=100%). This product is found to have an optical rotation$[\alpha9_{546} = +19.0°$ (C=1, H$_2$O).

What we claim is:

1. A process for racemization of an optically active lysine alkyl ester dihydrochloride, which comprises carrying out the reacting by heating under anhydrous conditions an optically active lysine alkyl ester, dihydrochloride at 100° to 250° C. under an atmosphere of hydrogen at a hydrogen pressure of 1 to 200 atmospheres.

2. A process according to claim 1, wherein the alkyl group of the lysine alkyl ester is an alkyl group having 1 to 4 carbon atoms.

3. A process according to claim 2, wherein the lysine alkyl ester is lysine methyl ester.

4. A process according to claim 2, wherein the lysine alkyl ester is lysine ethyl ester.

5. A process according to claim 1, wherein the reaction is carried out under an hydrogen pressure of 1 to 100 atm.

6. A process according to claim 1, wherein the reaction is carried out in a solvent.

7. A process according to claim 6, wherein the solvent is an alcohol corresponding to alkyl residue in the lysine alkyl ester to be racemized.

* * * * *